United States Patent [19]

Fozzard et al.

[11] 4,238,356

[45] Dec. 9, 1980

[54] DIACYLOXYBUTENE ISOMERIZATION CATALYSTS COMPRISING SELENIUM DIOXIDE AND CARBOXYLIC ACID

[75] Inventors: George B. Fozzard; John R. Norell, both of Bartlesville, Okla.

[73] Assignee: Phillips Petroleum Company, Bartlesville, Okla.

[21] Appl. No.: 62,389

[22] Filed: Jul. 31, 1979

Related U.S. Application Data

[62] Division of Ser. No. 841,780, Oct. 13, 1977, Pat. No. 4,182,901.

[51] Int. Cl.$^3$ .................. B01J 27/00; B01J 31/04; C07C 67/28; C07C 163/00
[52] U.S. Cl. .................. 252/430; 252/428; 252/431 C; 560/262; 260/550
[58] Field of Search ............. 260/607 R; 252/428, 252/430, 431 C, 439

[56] References Cited

U.S. PATENT DOCUMENTS

| | | | |
|---|---|---|---|
| 2,575,896 | 11/1951 | Smith et al. | 560/262 |
| 3,577,216 | 5/1971 | Weiss et al. | 252/439 |
| 3,715,389 | 2/1973 | Hoch et al. | 260/497 R |
| 3,755,423 | 8/1973 | Omoda et al. | 260/497 A |
| 3,778,468 | 12/1973 | Kollar | 260/497 R |
| 3,830,833 | 8/1974 | Shunsuke et al. | 560/262 |
| 3,872,163 | 3/1975 | Shimizu et al. | 560/262 |
| 4,095,030 | 6/1978 | Stapp | 560/262 |
| 4,121,039 | 10/1978 | Parthasarathy | 560/112 |

OTHER PUBLICATIONS

*Ind. Eng. Prod. Res. Develop*—vol. 9, No. 1, Mar. 1970, pp. 87–91, "Liquid Phase Oxidation of 1,3 Butadiene with Selenium Oxide"—Javaid et al.

*Industrial & Engineering Chemistry*—vol. 55, No. 12, Dec. 1963, pp. 18–26, "Catalytic Activity of Selenium'-'"—Kollonitsch et al.

*Primary Examiner*—P. E. Konopka

[57] ABSTRACT

Diacyloxyolefins are isomerized by contacting one or more diacyloxyolefins with a catalyst system comprising selenium dioxide and a suitable carboxylic acid. There can be additionally present in the catalyst system at least one compound selected from the group consisting of a carboxylic acid anhydride, a polar compound and an ionic reagent.

9 Claims, No Drawings

DIACYLOXYBUTENE ISOMERIZATION CATALYSTS COMPRISING SELENIUM DIOXIDE AND CARBOXYLIC ACID

This application is a division of copending application Ser. No. 841,780, filed Oct. 13, 1977, now U.S. Pat No. 4,182,901.

BACKGROUND OF THE INVENTION

This invention relates to the isomerization of diacyloxyolefins.

A number of chemicals can be made from diacyloxyolefins. More specifically, a diacyloxyolefin can easily be converted to various valuable chemicals such as diols, furans, and polyesters. For example, by means of various processes known in the art, 1,3-butadiene can be converted to a mixture of 1,4-diacloxy-2-butene and its isomer 1,2-diacloxy-3-butene. Since the 1,2-isomer is the more volatile of the two, the 1,4-isomer can be separated from the 1,2-isomer by fractional distillation. The 1,4-isomer can then be hydrogenated to remove the double bond and to produce 1,4-diacyloxybutane which can be converted to tetrahydrofuran by hydrolysis and cyclization. This overall process to convert 1,3-butadiene to tetrahydrofuran could be substantially simplified by including an isomerization step to convert the 1,2-isomer to the 1,4-isomer.

An object of this invention is to provide a process for isomerization of diacyloxyolefins.

Another object of this invention is to provide a catalyst system for isomerization of a diacyloxyolefin to the desired isomer.

The instant invention is suitable for the isomerization of diacyloxyolefins represented by the general formulas I and II shown below:

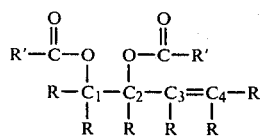

(I)

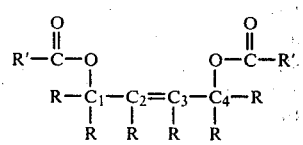

(II)

wherein each R is individually selected from the group consisting of hydrogen or an alkyl radical of from 1–4 carbon atoms, and wherein R' can be R or an aryl radical of from 6–10 carbon atoms, and wherein at least one of the R's attached to the carbon atoms numbered 1 and 4 in formulas I and II is hydrogen.

Further objects, advantages, details and embodiments of this invention will become apparent to those skilled in the art from the following detailed description of the invention, the examples, and the appended claims.

In accordance with the present invention there is provided a process for the isomerization of diacyloxyolefins which comprises contacting under isomerization conditions at least one diacyloxyolefin with a catalyst system formed by admixing selenium dioxide and a carboxylic acid represented by the general formula

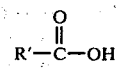

wherein R' is selected from the group consisting of hydrogen, and alkyl radical of from 1–4 carbon atoms, and an aryl radical of from 6–10 carbon atoms. Additionally present in the catalyst system can be at least one compound selected from the group consisting of a carboxylic acid anhydride, a polar compound, and an ionic reagent.

The instant invention also provides an isomerization system for converting diacyloxyolefins of general formula I to isomeric compounds of general formula II or for converting diacyloxyolefins of general formula II to isomeric compounds of general formula I. For example, 1,2-diacetoxy-3-butene can be isomerized to a mixture of 1,2-diacetoxy-3-butene and 1,4-diacetoxy-2-butene from which 1,4-diacetoxy-2-butene can be separated and 1,2-diacetoxy-3-butene recycled to the isomerization step. Likewise, 1,4-diacetoxy-2-butene can be isomerized to a mixture of 1,2-diacetoxy-3-butene and 1,4-diacetoxy-2-butene from which 1,2-diacetoxy-3-butene can be separated and 1,4-diacetoxy-2-butene recycled to the isomerization step. It is recognized that the maximum extent of isomerization achieved according to the instant invention will be limited according to the equilibrium composition for the system assuming that no steps are taken to upset the equilibrium. The position of the equilibrium can generally be determined by following the extent of isomerization with time when starting with a single isomeric compound or preferably utilizing separately both isomers in two such runs. For economic reasons, the equilibrium isomer composition need not be reached and the isomerization reaction can be terminated after a convenient time and the reaction product separated.

Compounds represented by general formulas I and II above are conveniently prepared by the oxidation of conjugated butadiene in the presence of a carboxylic acid represented by the general formula R'—CO₂H wherein R' is selected from the group consisting of hydrogen, an alkyl radical of from 1–4 carbon atoms, or an aryl radical of from 6–10 carbon atoms.

The diacyloxyolefins suitable for use in the invention can be selected from a large variety of compounds. Some examples of compounds represented by general formula I which can be employed in the instant invention include 1,2-diacetoxy-3-butene, 1,2-diacetoxy-3-methyl-3-butene, 1,2-diformyloxy-3-butene, 1,2-dibenzoxy-3-butene, 1,2-di-1-naphthoyloxy-3-butene, 1,2-dipropionyloxy-3-butene, 1,2-diacetoxy-2,3-dimethyl-3-butene. Some examples of compounds represented by general formula II which can be employed in the instant invention include 1,4-diacetoxy-2-butene, 1,4-diacetoxy-2-methyl-2-butene, 1,4-diformyloxy-2-butene, 1,4-dibenzoxy-2-butene, 1,4-di-1-naphthoyloxy-2-butene, 1,4-dipropionyloxy-2-butene, 1,4-diacetoxy-2,3-dimethyl-2-butene.

The diacyloxybutenes are a preferred group of reactants with the diacetoxybutenes being especially preferred because of availability, reactivity, and important utility.

Suitable mixtures, i.e., non-equilibrium mixtures, of isomeric compounds corresponding to formulas I and II can, of course, also be employed in the process of this invention. For example, the instant invention can be employed to treat non-equilibrium mixtures of isomers of types I and II noted above to enrich the mixture in one or the other isomer depending on the starting composition of the mixture. From a practical standpoint, it is envisioned that the instant invention will be of greatest benefit in the treatment of non-equilibrium mixtures.

The isomerization of the diacyloxyolefin described above is preferably achieved by contacting under isomerization conditions a diacyloxyolefin with a catalyst system formed by admixing selenium dioxide and a carboxylic acid represented by the general formula

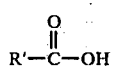

wherein R' is selected from the group consisting of hydrogen, an alkyl radical of from 1-4 carbon atoms, or an aryl radical of from 6-10 carbon atoms.

It is preferred for the practice of the isomerization of the instant invention that the R' in the carboxylic acid and in the diacyloxyolefin be the same.

Some examples of suitable carboxylic acids are acetic acid, formic acid, benzoic acid, 1-naphthoic acid, and propionic acid.

The most preferred carboxylic acid utilized in this invention is acetic acid.

The amount of carboxylic acid employed for the process of this invention is generally within the range of 0.005-100 liters per mole of diacyloxyolefin and preferably within the range of 0.1-10 liters per mole of diacyloxyolefin.

The amount of selenium dioxide employed for the process of this invention is generally within the range of 0.0001-0.4 moles per mole of diacyloxyolefin or mixture thereof and preferably within the range of 0.001-0.2 moles per mole of diacyloxyolefin. Higher levels of selenium dioxide may be used, but will not appreciably aid the isomerization.

In another embodiment of this invention, the isomerization system can also additionally have at least one compound selected from the group consisting of a carboxylic acid anhydride, a polar compound, and an ionic reagent present therein.

The suitable carboxylic acid anhydride is represented by the general formula

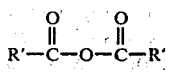

wherein R' is selected from the group consisting of hydrogen, alkyl radicals of from 1-4 carbon atoms, or an aryl radical of from 6-10 carbon atoms.

The R' in the carboxylic acid anhydride should be the same as that in the starting diacyloxyolefin.

Some examples of suitable carboxylic acid anhydrides for the isomerization of the instant invention include acetic anhydride, benzoic anhydride, 1-naphthoic anhydride, propionic anhydride.

The preferred carboxylic acid anhydride utilized in this invention is acetic anhydride.

The amount of carboxylic acid anhydride employed for the process of this invention is generally within the range of 0.005-100 liters per mole of diacyloxyolefin and preferably within the range of 0.1-10 liters per mole of diacyloxyolefin.

The polar compounds should have a dielectric constant of at least 10 when measured within the temperature range of 20°-30° C. and should be essentially inert under the isomerization conditions.

Some examples of suitable polar compounds are those selected from the group consisting of pyridine, 1-methyl-2-pyrrolidinone, N,N-dimethylformamide, N,N-dimethylacetamide, hexamethylphosphoramide, benzonitrile, acetonitrile, dimethyl sulfoxide, sulfolane.

The amount of polar compound employed for the process of this invention is generally within the range of 0.005-100 liters per mole of diacyloxyolefin and preferably within the range of 0.1-10 liters per mole of diacyloxyolefin.

The ionic reagent utilized is selected from the group consisting of the alkali metal, alkaline earth metal, and ammonium hydroxides or salts of a carboxylic acid represented by the general formula

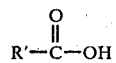

wherein R' is selected from the group consisting of hydrogen, an alkyl radical of from 1-4 carbon atoms, or an aryl radical of from 6-10 carbon atoms.

As used herein, the term "alkali metal" denotes the metals lithium, sodium, potassium, rubidium, and cesium while the term "alkaline earth metal" denotes the metals beryllium, magnesium, calcium, strontium, and barium.

Some examples of suitable ionic reagents include sodium acetate, lithium formate, potassium benzoate, cesium propionate, ammonium acetate, sodium butyrate, potassium 1-naphthoate, beryllium acetate, magnesium formate, calcium benzoate, strontium acetate, barium acetate, ammonium benzoate, lithium hydroxide, sodium hydroxide, potassium hydroxide, cesium hydroxide, ammonium hydroxide, beryllium hydroxide, magnesium hydroxide, calcium hydroxide, strontium hydroxide, barium hydroxide.

The amount of ionic reagent employed for the process of this invention is not critical and can be selected from a relatively broad range of amounts. Generally the amount is within the range of 0.001-5 moles per mole of starting diacyloxyolefin or mixture thereof with a preferable range of 0.05-2 moles per mole of diacyloxyolefin.

R' in the carboxylate salt should be the same as that in the starting diacyloxyolefin. For example, an acetate salt should be used when a diacetoxyolefin is to be isomerized.

The isomerization reaction of this invention is carried out at a temperature that can be selected over a broad range. Generally, the temperature ranges from about 150° C. to about 360° C., preferably from about 175° C. to about 250° C.

The time utilized for the isomerization reaction will depend on temperature, the component concentration, and on the extent of isomerization desired. In some instances, the reaction may be conducted for a few minutes or for as long as 24 hours and longer. Thus, in most instances, reaction time is not considered to be a significant parameter of the invention.

The isomerization reaction according to this invention is preferably carried out at a pressure sufficient to maintain the system in the liquid phase which often is autogenous pressure. However, the reaction can be conducted in the presence of an added inert gas such as nitrogen at atmospheric or super-atmospheric pressure. The latter condition may be employed in those instances wherein a relatively low boiling material is used at a relatively high temperature in order to maintain a predominantly liquid phase system.

In a presently preferred embodiment of this invention the isomerization reaction mixture is homogeneous as compared to a heterogenous mixture. In any event, conventional liquid phase mixing procedures can be utilized during the reaction period in this invention.

The presence of water in the reaction mixture can give rise to the production of hydroxyolefin compounds which may be very difficult to separate from the diacyloxyolefins. For this reason, it is preferred to operate under essentially anhydrous conditions.

The isomerization reaction product obtained according to the instant invention can be filtered to remove any solid material and subjected to fractional distillation to separate the desired diacyloxyolefin. The other diacyloxyolefin can then be recycled.

When using a polar compound that has appreciable water solubility, it may be desirable to extract the reaction mixture with water and thereafter separate the diacyloxyolefin mixture by fractional distillation. Said water extraction should be conducted under conditions which do not promote hydrolysis of diacyloxyolefins, e.g., at temperatures below about 70° C. Furthermore, traces of water should be removed from the residual diacyloxyolefins before distillation in order to avoid hydrolysis. Other suitable separation methods can be employed in the separation of the reaction mixture components.

Generally, this invention will find broadest utility in the isomerization of type I compounds to type II compounds. Type II compounds can be hydrogenated and cyclized to tetrahydrofurans or pyrrolidones. Alternatively, they can be hydrogenated then hydrolyzed to 1,4-diols which are useful as solvents or monomers in the preparation of polyesters of polyurethanes. Especially important in this regard is 1,4-butanediol which is employed in the production of polybutylene terephthalate, an important polyester resin with highly desirable properties.

However, this invention can also be utilized to isomerize type II compounds to type I compounds. The type I compounds can be hydrogenated and hydrolyzed to yield vicinal diols that are useful as sensitizers and fog inhibitors for photographic emulsions, for the production of polyurethane coatings having improved viscosity stability, and for the production of polyester films with improved stability for use in electrical condensers.

The following Examples will further illustrate the invention.

EXAMPLE I

A series of runs were conducted according to the instant invention using cis-1,4-diacetoxy-2-butene.

In each run the reaction was carried out in a 120 ml Fischer-Porter aerosol compatibility bottle equipped with a magnetic stirrer, thermocouple, and heating mantle. The bottle was charged with 150 ml acetic acid, 10 ml acetic anhydride, 1.0 g (42 mmole) lithium hydroxide, 1.1 g (10 mmole) selenium dioxide, and 8.7 g (51 mmole) cis-1,4-diacetoxy-2-butene. Also added to the above was 2.0 g 1,3-diacetoxypropane—an internal standard for gas-liquid chromatographic (glc) analysis. This glc standard was not a necessary component to effect isomerization.

Each reaction mixture was heated to about 200° C. and samples were taken at several points during the reaction for later analysis. The samples taken during the reaction and the final reaction mixture were analyzed directly by gas-liquid chromatography (glc) and the results are shown in Table I.

TABLE I

| Run No. | Temp., °C. | Press.,(a) psig (MPa) | Time,(b) min. | 1,2-diacetoxy-3-butene, % | cis-1,4-diacetoxy-2-butene, % | trans-1,4-diacetoxy-2-butene, % |
|---|---|---|---|---|---|---|
| 1 | 185 | 90(0.62) | 15 | 7.6 | 92.4 | — |
|   | 200 | 84(0.58) | 131 | 9.3 | 90.7 | — |
|   | 200 | 86(0.59) | 247 | 10.2 | 81.9 | 7.9 |
|   | (c) |  |  | 12.4 | 79.9 | 7.8 |
| 2 | 200 | 82(0.56) | 64 | 18 | 75 | 7 |
|   | 195 | 80(0.55) | 194 | 18 | 72 | 11 |
|   | 195 | 85(0.59) | 324 | 21 | 64 | 15 |
|   | (d) |  |  | 22 | 59 | 20 |

(a)MPa = mega Pascale
(b)Amount of time after the reaction mixture reached a temperature of about 200° C.
(c)Reaction mixture at the end of the reaction.
(d)Reaction mixture after standing overnight at room temperature.

The results of Table I demonstrate that the system of the instant invention isomerized cis-1,4-diacetoxy-2-butene to 1,2-diacetoxy-3-butene. Under the reaction conditions there was also some isomerization of cis-1,4-diacetoxy-2-butene to trans-1,4-diacetoxy-2-butene.

The isomerization of diacyloxyolefins is an equilibrium process and an equilibrium mixture can be approached from either isomer. Since the isomerization of cis-1,4-diacetoxy-2-butene to 1,2-diacetoxy-3-butene under the conditions of this invention has been established, the isomerization of 1,2-diacetoxy-3-butene to 1,4-diacetoxy-2-butene is expected to occur under these isomerization conditions.

EXAMPLE II

A further run was carried out in essentially the same manner as in Runs 1 and 2 of Example I except that selenium dioxide was not included. The same type of vessel as in Example I was charged with 80 ml acetic acid, 5 ml acetic anhydride, 2.0 g (84 mmole) lithium hydroxide, 16.2 g. (94 mmole) cis-1,4-diacetoxy-2-butene, and 2.0 g. 1,3-diacetoxypropane (an internal glc standard). The reaction mixture was heated (about 200° C.) with stirring for 393 minutes.

Analysis (glc) of samples taken during the run and of the final reaction mixture showed no detectable amounts of 1,2-diacetoxy-3-butene. There was no significant amount of cis-1,4-diacetoxy-2-butene to trans-1,4-diacetoxy-2-butene isomerization under the reaction-conditions.

The results of this control run show that essentially no isomerization of cis-1,4-diacetoxy-2-butene to 1,2-diacetoxy-3-butene occurs in the absence of selenium dioxide.

Reasonable variations and modifications, which will become apparent to those skilled in the art, can be made in this invention without departing from the spirit and scope thereof.

What is claimed is:

1. A catalyst composition comprising the reaction product of
    (a) a carboxylic acid represented by the general formula:

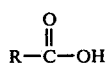

wherein R is selected from the group consisting of hydrogen, alkyl having from 1 to 4 carbon atoms, and aryl from 6 to 10 carbon atoms:
    (b) selenium dioxide;
    (c) an ionic reagent selected from the group consisting of alkali metal hydroxide, alkaline earth metal hydroxide, ammonium hydroxide and a salt of said carboxylic acid; and
    (d) an acid anhydride represented by the formula

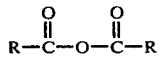

wherein each R is as defined above and is individually selected.

2. A composition as in claim 1 further comprising a polar compound having a dielectric constant of at least 10 when measured within a temperature range of 20°-30° C. in combination with said carboxylic acid, said selenium dioxide, said ionic reagent and said acid anhydride.

3. A composition as in claim 2 wherein said polar compound is selected from the group consisting of pyridine, 1-methyl-2-pyrrolidinone, N,N-dimethylformamide, benzonitrile, acetonitrile, dimethyl sulfoxide and sulfolane.

4. A composition as in claim 3 comprising the reaction product of from 0.005 to 100 liters of said carboxylic acid with from 0.001–0.4 moles of selenium dioxide, and at least one of 0.001–5 moles of said ionic reagent, from 0.005–100 liters of said acid anhydride, and from 0.005–100 liters of said polar compound.

5. A composition as in claim 4 comprising the reaction product of from 0.1 to 10 liters of said carboxylic acid with from 0.001 to 0.2 moles of selenium dioxide and at least one of from 0.05 to 2 moles of said ionic reagent, from 0.1 to 10 liters of said polar compound and from 0.05 to 10 liters of said polar compound.

6. A composition as in claim 5 wherein said carboxylic acid is selected from the group consisting of formic acid, acetic acid, propionic acid, benzoic acid, and 1-napthoic acid.

7. A composition as in claim 6 wherein said ionic reagent is selected from the group consisting of sodium acetate, lithium formate, potassium benzoate, cesium propionate, ammonium acetate, sodium butyrate, potassium 1-naphthoate, beryllium acetate, magnesium formate, calcium benzoate, strontium acetate, barium acetate, ammonium benzoate, lithium hydroxide, sodium hydroxide, potassium hydroxide, cesium hydroxide, ammonium hydroxide, beryllium hydroxide, magnesium hydroxide, calcium hydroxide, strontium hydroxide, and barium hydroxide.

8. A composition as in claim 7 wherein said acid anhydride is selected from the group consisting of acetic anhydride, benzoic anhydride, 1-naphthoic anhydride and propionic anhydride.

9. A composition as in claim 8 wherein said carboxylic acid is acetic acid, said ionic reagent is lithium hydroxide, said acid anhydride is acetic anhydride, and said polar compound is pyridine.

* * * * *

UNITED STATES PATENT AND TRADEMARK OFFICE
CERTIFICATE OF CORRECTION

PATENT NO. : 4,238,356
DATED : December 9, 1980
INVENTOR(S) : George B. Fozzard et al It is certified that error appears in the above-identified patent and that said Letters Patent is hereby corrected as shown below:

Column 7, lines 14 and 15 (Claim 1, lines 1 and 2, delete "comprising the reaction product of" and substitute therefor --- formed by admixing ---.

Column 8, lines 8 and 9 (Claim 4, lines 1 and 2), delete "comprising the reaction product of" and substitute therefor --- formed by admixing ---.

Column 8, lines 14 and 15 (Claim 5, lines 1 and 2), delete "comprising the reaction product of" and substitute therefor --- formed by admixing ---.

Column 8, line 19 (line 4) delete "0.05" and substitute therefor --- 0.1 ---.

Column 8, line 19 (line 5) delete "polar compound" and substitute therefor --- acid anhydride ---.

Signed and Sealed this

Nineteenth Day of April 1983

[SEAL]

Attest:

GERALD J. MOSSINGHOFF

*Attesting Officer*     *Commissioner of Patents and Trademarks*